USOO6750269B2

(12) United States Patent
Smith

(10) Patent No.: US 6,750,269 B2
(45) Date of Patent: Jun. 15, 2004

(54) INK JET PRINTING WITH INKS CONTAINING CYCLIC SILOXANES

(75) Inventor: Thomas W. Smith, Penfield, NY (US)

(73) Assignee: Xerox Corporation, Stamford, CT (US)

( * ) Notice: Subject to any disclaimer, the term of this patent is extended or adjusted under 35 U.S.C. 154(b) by 208 days.

(21) Appl. No.: 10/007,728

(22) Filed: Nov. 13, 2001

(65) Prior Publication Data

US 2003/0096886 A1 May 22, 2003

(51) Int. Cl.$^7$ .................. C09D 11/02; C08G 77/06; C08G 77/04; C08L 83/04; C08L 83/06
(52) U.S. Cl. .................. 523/160; 106/31.28; 106/31.6; 524/588; 528/12; 528/21; 528/37
(58) Field of Search ................... 523/160, 161; 106/31.28, 31.6; 524/548, 588; 528/12, 21, 31, 35, 37

(56) References Cited

U.S. PATENT DOCUMENTS

| | | | | | |
|---|---|---|---|---|---|
| 3,041,362 | A | * | 6/1962 | Merker | 556/434 |
| 3,427,338 | A | * | 2/1969 | Frye | 556/434 |
| 3,481,898 | A | * | 12/1969 | Davies et al. | 528/14 |
| 5,750,594 | A | | 5/1998 | Page et al. | 523/161 |
| 5,820,932 | A | | 10/1998 | Hallman et al. | 427/261 |
| 5,889,083 | A | * | 3/1999 | Zhu | 523/161 |
| 6,492,480 | B1 | * | 12/2002 | Nagashima et al. | 528/19 |
| 6,534,587 | B1 | * | 3/2003 | Tapsak et al. | 524/588 |

FOREIGN PATENT DOCUMENTS

| | | | |
|---|---|---|---|
| EP | 465262 A2 | * | 1/1992 |
| EP | 0879857 A2 | | 5/1998 |
| JP | 10-295727 | | 4/2000 |
| JP | 10-332856 | | 6/2000 |

OTHER PUBLICATIONS

J.C. Salamone et al., "Polymerization of Vinylpridinium Salts. X. Copolymerization Studies of Cationic–Anionic Monomer Pairs," *Journal of Polymer Science: Polymer Symposium*, vol. 64, p. 229 (1978).
J.N. Braham et al., "New Monomers and Polymers. V. Study of the Spontaneous Polymerization of 5–Ethoxycarbonyl–3–formyl–2–pyrazoline," *Journal of Polymer Science: Polymer Chemistry Edition*, vol. 15, p. 829 (1977).
V. Konsulov et al., "Spontaneous Polymerization of Maleic Anhydride with 1–Vinylimidazole and 2–Methyl–1–vinylimidazole," *Khim. Ind. (Sofia)*, vol. 5, p. 212 (1980).
V.S. Savostyanov et al., "The Preparation and Reactivity of Metal–Containing Monomers. 21–Spontaneous Polymerization of Acrylamide Coordinated with Metal Nitrates," *Izv. Akad. Nauk. Ser. Khim*, vol. 9, p. 2073 (1992).
D.A. Loy et al., "Phenylene–Bridged Cyclic Siloxanes as Precursors to Nonshrinking Sol–Gel Systems and Their Use as Encapsulants," *Angew. Chem. Int. Ed.*, vol. 38, No. 4, p. 555 (1999).
"Expanding Monomers: Synthesis, Characterization, and Applications", R.K. Sadhir and R.M. Luck, eds., CRC Press (Boca Raton; 1992).
J.C. Salamone et al., "Polymerization of Vinylpyridinium Salts. IX. Preparation of Monomeric Salt Pairs," *J. Polym. Sci.: Polymer Letters Edition*, vol. 15, p. 487 (1977).
V.N. Khmelenko et al., "Polymerization of N,N–Dimethylaminoethyl Methacrylate in the Presence of p–Toluenesulfonic Acid," *Uzb. Khim. Zh.*, vol. 1, p. 56 (1985).
V.N. Kizhnyaev et al., "Water–Soluble and Water–Swelling Polymeric Salts of 5–Vinyltetrazole," *Zh. Prikl. Khim (Lenigrad)*, vol. 63, No. 12, p. 2721 (1990).
Copending Application U.S. Ser. No. (not yet assigned); filed concurrently herewith, entiitled "Ink Jet Printing With Inks Containing Cationic–Anionic Monomer Pairs," by Thomas W. Smith.
J.C. Salmone et al., "Polymerization of Vinylpridinum Salts." Journal of Polymer Science: Polymer Symposium, vol. 64, p. 229 (1978).

* cited by examiner

*Primary Examiner*—Callie Shosho
(74) *Attorney, Agent, or Firm*—Judith L. Byorick

(57) ABSTRACT

Disclosed is an ink composition comprising a liquid ink vehicle, a colorant, and a cyclic siloxane monomer composition capable of undergoing a ring-opening polymerization process upon contact with an anionic base. Another embodiment of the present invention is directed to a process which comprises (a) providing (1) a first ink comprising water and at least one cyclic siloxane monomer composition; and (2) a second ink comprising a liquid ink vehicle and an anionic base capable of causing the cyclic siloxane monomer to polymerize upon contact therewith, wherein at least one of the first ink and the second ink further comprises a colorant; (b) incorporating into an ink jet printing apparatus at least one of the first ink and the second ink; (c) applying the first ink onto a substrate; and (d) applying the second ink onto the substrate; wherein at least one of the first ink and the second ink is ejected from the ink jet printing apparatus in an imagewise pattern onto the substrate; and wherein the process results in at least some portions of the substrate bearing images formed from both the first ink and the second ink, said portions forming a printed image containing a polysiloxane and the colorant.

20 Claims, No Drawings

INK JET PRINTING WITH INKS CONTAINING CYCLIC SILOXANES

Copending Application U.S. Ser. No. 10/010,491, filed concurrently herewith, entitled "ink Jet Printing with inks Containing Cationic-Anionic Monomer Pairs," with the named inventor Thomas W. Smith, the disclosure of which is totally incorporated herein by reference, discloses a process which comprises (a) incorporating into an ink jet printing apparatus (1) a first ink comprising water and at least one anionic monomer; and (2) a second ink comprising wafer and at least one cationic monomer, wherein the anionic monomer and the cationic monomer are selected so that upon contact of the anionic monomer with the cationic monomer, spontaneous polymerization or copolymerization of at least one of the anionic monomer or the cationic monomer occurs, and wherein at least one of the first ink and the second ink further comprises a colorant (b) causing droplets of the first ink to be ejected In an imagewise pattern onto the substrate; and (c) causing droplets of the second ink to be ejected in an imagewise pattern onto the substrate; wherein the process results in at least same portions of the substrate bearing images formed from both the first ink and the second ink, said portions forming a printed image containing the colorant and a polymer formed from at least one of the anionic monomer or the cationic monomer. Similar processes are disclosed with N,N-dimethylaminoethyl methacrylate and p-toluene sulfonic acid, with acrylamide and a multivalent metal nitrate salt and with 5-vinyl tetrazole and an amine base.

BACKGROUND OF THE INVENTION

The present invention is directed to ink jet printing compositions and processes. More specifically, the present invention is directed to ink jet printing compositions and processes that enable rapid drying and fixation of marking fluids to recording substrates. One embodiment of the present invention is directed to an ink composition comprising a liquid ink vehicle, a colorant, and a cyclic siloxane monomer composition capable of undergoing a ring-opening polymerization process upon contact with an anionic base. Another embodiment of the present invention is directed to a process which comprises (a) providing (1) a first ink comprising water and at least one cyclic siloxane monomer composition; and (2) a second ink comprising a liquid ink vehicle and an anionic base capable of causing the cyclic siloxane monomer to polymerize upon contact therewith, wherein at least one of the first ink and the second ink further comprises a colorant; (b) incorporating into an ink jet printing apparatus at least one of the first ink and the second ink; (c) applying the first ink onto a substrate; and (d) applying the second ink onto the substrate; wherein at least one of the first ink and the second ink is ejected from the ink jet printing apparatus in an imagewise pattern onto the substrate; and wherein the process results in at least some portions of the substrate bearing images formed from both the first ink and the second ink, said portions forming a printed image containing a polysiloxane and the colorant.

Ink jet printing systems generally are of two types: continuous stream and drop-on-demand. In continuous stream ink jet systems, ink is emitted in a continuous stream under pressure through at least one orifice or nozzle. The stream is perturbed, causing it to break up into droplets at a fixed distance from the orifice. At the break-up point, the droplets are charged in accordance with digital data signals and passed through an electrostatic field which adjusts the trajectory of each droplet in order to direct it to a gutter for recirculation or a specific location on a recording medium. In drop-on-demand systems, a droplet is expelled from an orifice directly to a position on a recording medium in accordance with digital data signals. A droplet is not formed or expelled unless it is to be placed on the recording medium.

Since drop-on-demand systems require no ink recovery, charging, or deflection, the system is much simpler than the continuous stream type. There are two types of drop-on-demand ink jet systems. One type of drop-on-demand system has as its major components an ink filled channel or passageway having a nozzle on one end and a piezoelectric transducer near the other end to produce pressure pulses. the relatively large size of the transducer prevents close spacing of the nozzles, and physical limitations of the transducer result in low ink drop velocity. Low drop velocity seriously diminishes tolerances for drop velocity variation and directionality, thus impacting the system's ability to produce high quality copies. Drop-on-demand systems which use piezoelectric devices to expel the droplets also suffer the disadvantage of a slow printing speed.

Another type of drop-on-demand system is known as thermal ink jet, or bubble jet, and produces high velocity droplets and allows very close spacing of nozzles. The major components of this type of drop-on-demand system are an ink filled channel having a nozzle on one end and a heat generating resistor near the nozzle. Printing signals representing digital information originate an electric current pulse in a resistive layer within each ink passageway near the orifice or nozzle, causing the ink in the immediate vicinity to evaporate almost instantaneously and create a bubble. The ink at the orifice is forced out as a propelled droplet as the bubble expands. When the hydrodynamic motion of the ink stops, the process is ready to start all over again. With the introduction of a droplet ejection system based upon thermally generated bubbles, commonly referred to as the "bubble jet" system, the drop-on-demand ink jet printers provide simpler, lower cost devices than their continuous stream counterparts, and yet have substantially the same high speed printing capability.

The operating sequence of the bubble jet system begins with a current pulse through the resistive layer in the ink filled channel, the resistive layer being in close proximity to the orifice or nozzle for that channel. Heat is transferred from the resistor to the ink. The ink becomes superheated far above its normal boiling point, and for water based ink, finally reaches the critical temperature for bubble formation or nucleation of around 280° C. Once nucleated, the bubble or water vapor thermally isolates the ink from the heater and no further heat can be applied to the ink. This bubble expands until all the heat stored in the ink in excess of the normal boiling point diffuses away or is used to convert liquid to vapor, which removes heat due to heat of vaporization. The expansion of the bubble forces a droplet of ink out of the nozzle, and once the excess heat is removed, the bubble collapses on the resistor. At this point, the resistor is no longer being heated because the current pulse has passed and, concurrently with the bubble collapse, the droplet is propelled at a high rate of speed in a direction towards a recording medium. The resistive layer encounters a severe cavitational force by the collapse of the bubble, which tends to erode it. Subsequently, the ink channel refills by capillary action. This entire bubble formation and collapse sequence occurs in about 10 microseconds. The channel can be refired after 100 to 500 microseconds minimum dwell time to enable the channel to be refilled and to enable the dynamic refilling factors to become somewhat dampened. Thermal ink jet processes are well known and are described in, for example, U.S. Pat. Nos. 4,601,777, 4,251,824, 4,410,899, 4,412,224, and 4,532,530, the disclosures of each of which are totally incorporated herein by reference.

Acoustic ink jet printing processes are also known. As is known, an acoustic beam exerts a radiation pressure against objects upon which it impinges. Thus, when an acoustic beam impinges on a free surface (i.e., liquid/air interface) of a pool of liquid from beneath, the radiation pressure which it exerts against the surface of the pool may reach a sufficiently high level to release individual droplets of liquid from the pool, despite the restraining force of surface tension. Focusing the beam on or near the surface of the pool intensifies the radiation pressure it exerts for a given amount of input power. These principles have been applied to prior ink jet and acoustic printing proposals. For example, K. A. Krause, "Focusing ink Jet Head," *IBM Technical Disclosure Bulletin*, Vol. 16, No. 4, September 1973, pp. 1168–1170, the disclosure of which is totally incorporated herein by reference, describes an ink jet in which an acoustic beam emanating from a concave surface and confined by a conical aperture was used to propel ink droplets out through a small ejection orifice. Acoustic ink printers typically comprise one or more acoustic radiators for illuminating the free surface of a pool of liquid ink with respective acoustic beams. Each of these beams usually is brought to focus at or near the surface of the reservoir (i.e., the liquid/air interface). Furthermore, printing conventionally is performed by independently modulating the excitation of the acoustic radiators in accordance with the input data samples for the image that is to be printed. This modulation enables the radiation pressure which each of the beams exerts against the free ink surface to make brief, controlled excursions to a sufficiently high pressure level for overcoming the restraining force of surface tension. That, in turn, causes individual droplets of ink to be ejected from the free ink surface on demand at an adequate velocity to cause them to deposit in an image configuration on a nearby recording medium. The acoustic beam may be intensity modulated or focused/defocused to control the ejection timing, or an external source may be used to extract droplets from the acoustically excited liquid on the surface of the pool on demand. Regardless of the timing mechanism employed, the size of the ejected droplets is determined by the waist diameter of the focused acoustic beam. Acoustic ink printing is attractive because it does not require the nozzles or the small ejection orifices which have caused many of the reliability and pixel placement accuracy problems that conventional drop-on-demand and continuous stream ink jet printers have suffered. The size of the ejection orifice is a critical design parameter of an ink jet because it determines the size of the droplets of ink that the jet ejects. As a result, the size of the ejection orifice cannot be increased, without sacrificing resolution. Acoustic printing has increased intrinsic reliability because there are no nozzles to clog. As will be appreciated, the elimination of the clogged nozzle failure mode is especially relevant to the reliability of large arrays of ink ejectors, such as page width arrays comprising several thousand separate ejectors. Furthermore, small ejection orifices are avoided, so acoustic printing can be performed with a greater variety of inks than conventional ink jet printing, including inks having higher viscosities and inks containing pigments and other particulate components. It has been found that acoustic ink printers embodying printheads comprising acoustically illuminated spherical focusing lenses can print precisely positioned pixels (i.e., picture elements) at resolutions which are sufficient for high quality printing of relatively complex images. It has also has been discovered that the size of the individual pixels printed by such a printer can be varied over a significant range during operation, thereby accommodating, for example, the printing of variably shaded images. Furthermore, the known droplet ejector technology can be adapted to a variety of printhead configurations, including (1) single ejector embodiments for raster scan printing, (2) matrix configured ejector arrays for matrix printing, and (3) several different types of pagewidth ejector arrays, ranging from single row, sparse arrays for hybrid forms of parallel/serial printing to multiple row staggered arrays with individual ejectors for each of the pixel positions or addresses within a pagewidth image field (i.e., single ejector/pixel/line) for ordinary line printing. Inks suitable for acoustic ink jet printing typically are liquid at ambient temperatures (i.e., about 25° C.), but in other embodiments the ink is in a solid state at ambient temperatures and provision is made for liquefying the ink by heating or any other suitable method prior to introduction of the ink into the printhead. Images of two or more colors can be generated by several methods, including by processes wherein a single printhead launches acoustic waves into pools of different colored inks. Further information regarding acoustic ink jet printing apparatus and processes is disclosed in, for example, U.S. Pat. Nos. 4,308,547, 4,697, 195, 5,028,937, 5,041,849, 4,751,529, 4,751,530, 4,751,534, 4,801,953, and 4,797,693, the disclosures of each of which are totally incorporated herein by reference. The use of focused acoustic beams to eject droplets of controlled diameter and velocity from a free-liquid surface is also described in *J. Appl. Phys.*, vol. 65, no. 9 (May 1, 1989) and references therein, the disclosure of which is totally incorporated herein by reference.

Other known droplet ejectors include those of the type disclosed in, for example, U.S. Pat. No. 6,127,198, the disclosure of which is totally incorporated herein by reference.

J. C. Salamone et al., "Polymerization of Vinylpyridinium Salts. X. Copolymerization Studies of Cationic-Anionic Monomer Pairs," *Journal of Polymer Science: Polymer Symposium*, Vol. 64, p. 229 (1978), the disclosure of which is totally incorporated herein by reference, discloses an investigation of ion pair copolymers between the cationic 4-vinylpyridinium moiety and the anionic vinylsulfonate, 2-acrylamido-2-methylpropanesulofonate, and p-styrenesulfonate. The results of the spontaneous polymerization suggest that for 4-vinylpyridinium vinylsulfonate, only the cationic moiety is polymerized, whereas for 4-vinylpyridinium 2-acrylamido-2-methylpropanesulfonate, two homopolymers or a block copolymer apparently result, and for 4-vinylpyridinium p-styrenesulfonate, an alternating copolymer appears to be obtained.

J. N. Braham et al., "New Monomers and Polymers. V. Study of the Spontaneous Polymerization of 5-Ethoxycarbonyl-3-formyl-2-pyrazoline," Journal of Polymer Science: Polymer Chemistry Edition, Vol. 15, p. 829 (1977), the disclosure of which is totally incorporated herein by reference, discloses that the 3-formyl-2-pyrazolines obtained by 1–3 dipolar additions of diazoesters to acrolein are unstable and smoothly polymerize through the aldehyde group to a polyacetal polymer. On the basis of spectroscopic data, the structure of the isolated polymers is described, along with their properties and a polymerization mechanism. It is proposed that a nucleophilic attack of a heterocyclic amino nitrogen on another monomer formyl group leads to an internal ion pair, and that this latter promotes a polycondensation of other aldehydic units according to an anionic type of propagation. The results are polyacetal polymers of low molecular weight with conservation of the heterocyclic framework. Numerous side reactions, however, are possible and account for the relatively low molecular weights observed.

V. Konsulov et al., "Spontaneous Polymerization of Maleic Anhydride with 1-Vinylimidazole and 2-Methyl-1-vinylimidazole," *Khim. Ind. (Sofia)*, Vol. 5, p. 212 (1980), the disclosure of which is totally incorporated herein by reference, discloses the spontaneous polymerization of maleic anhydride with imidazole derivatives which was related to an electron donor-acceptor interaction between the monomers leading to the formation of polymers with a carbonylvinylene structure and imidazole ring-containing end groups which act as polymerization catalysts.

V. S. Savostyanov et al., "the Preparation and Reactivity of Metal-Containing Monomers. 21. Spontaneous Polymerization of Acrylamide Coordinated with Metal Nitrates," *Izv. Akad. Nauk, Ser. Khim*, Vol. 9, p. 2073 (1992), the disclosure of which is totally incorporated herein by reference, discloses acrylamide complexes with Cr(III), Bi(III), Pb(II), and Ca(II) nitrates that undergo spontaneous polymerization in concentrated aqueous solutions at about 20°, forming water-containing glassy polymers. The polymerization time varies from several hours to several days depending on the reaction conditions and the nature of the metal nitrate. The product contains water soluble and water insoluble fractions. The insoluble fraction consists of polyacrylamide free of metal compounds. The possibility of spontaneous copolymerization of I-metal nitrate complexes with other water soluble monomers is established.

U.S. Pat. No. 5,820,932 (Hallman et al.), the disclosure of which is totally incorporated herein by reference, discloses the use of ink jet liquid droplets from one or more printer heads to form an image upon the surface of a printing plate corresponding to digital information depicting the image as provided by a digital computer system which is in digital communication with the printer heads. The droplets from the printer head comprise resin forming reactants which polymerize on the plate surface, alone or in combination with reactants precoated on the plate, to form a printable hard resin image. The resin image so formed provides a lithographic printing plate useful for extended print runs.

D. A. Loy et al., "Phenylene-Bridged Cyclic Siloxanes as Precursors to Nonshrinking Sol-Gel Systems and their Use as Encapsulants," *Angew. Chem. Int. Ed.*, Vol. 38, No. 4, p. 555 (1999), the disclosure of which is totally incorporated herein by reference, discloses the preparation of a new class of sol-gel processed, hybrid organic-inorganic materials based on the ring opening polymerization of cyclic siloxane monomers bearing one or more 2,2,5,5-tetramethyl-2,5-disilaoxacyclopentane groups.

*Expanding Monomers: Synthesis, Characterization, and Applications*, R. K. Sadhir and R. M. Luck, eds., CRC Press (Boca Raton, 1992), the disclosure of which is totally incorporated herein by reference, discloses ring opening polymerization reactions at pages 10 to 15.

J. C. Salamone et al., "Polymerization of Vinylpyridinium Salts. IX. Preparation of Monomeric Salt Pairs," *J. Polym. Sci.: Polymer Letters Edition*, Vol. 15, p. 487 (1977), the disclosure of which is totally incorporated herein by reference, discloses the preparation of vinylic cationic-anionic monomer pairs.

V. N. Khmelenko et al., "Polymerization of N,N-Dimethylaminoethyl Methacrylate in the Presence of p-Toluenesulfonic Acid," *Uzb. Khim. Zh.*, Vol. 1, p. 56 (1985), the disclosure of which is totally incorporated herein by reference, discloses the addition of p-toluenesulfonic acid to a solution of (dimethylamino)ethyl methacrylate which resulted in spontaneous polymerization of the (dimethylamino)ethyl methacrylate. The obtained polymer had polyelectrolyte properties as indicated by plots of reduced viscosity versus concentration. The yield of the polymer was maximized when the two reactants were at an equimolar ratio. The rate of the polymerization decreased on passing from solutions in ethanol to aqueous ethanol and to water.

V. N. Kizhnyaev et al., "Water-Soluble and Water-Swelling Polymeric Salts of 5-Vinyltetrazole," *Zh. Prikl. Khim* (Leningrad), Vol. 63, No. 12, p. 2721 (1990), the disclosure of which is totally incorporated herein by reference, discloses the reaction of 5-vinyltetrazole with amines ($NH_3$, $H_2NNH_2$, $Me_3N$, $Et_2N$, $Et_3N$) in solution, which occurred with salt formation and spontaneous polymerization. The yield of polymeric salt was highest at equimolar reactant ratios. The polymer contained 5-vinyltetrazole units in both the salt and nonsalt form, with the ratio of the two forms being independent of amine nature or polymerization conditions. The polymeric salts exhibited typical polyelectrolyte properties in aqueous solutions and were capable of forming hydrogels with a high degree of water absorption. The rate and degree of swelling of the salts in water increased with increasing content of salt units in the polymer.

Japanese Patent Publication JP 00158793, the disclosure of which is totally incorporated herein by reference, discloses an ink composition containing at least a titanium oxide, an oligomer or a monomer, and an aqueous solvent. A reaction liquid contains at least a polymerization initiator, a monomer or an oligomer, and an aqueous solvent. When the composition or the reaction liquid contains the oligomer, the other contains the monomer. In this case, the composition is adhered to a recording medium earlier than the liquid.

Japanese Patent Publication JP 00119574, the disclosure of which is totally incorporated herein by reference, discloses a method for ink jet printing comprising the use of an ink composition essentially comprising a colorant, an oligomer or the corresponding monomer, and an aqueous medium, and a reactive solution essentially comprising a polymerization initiator, the monomer or oligomer, and an aqueous medium, wherein when the ink composition or reaction solution contains the oligomer, the other party contains the monomer.

While known compositions and processes are suitable for their intended purposes, a need remains for improved inks and processes for ink jet printing. In addition, a need remains for ink jet compositions and processes that enable rapid drying times of inks on substrates. Further, a need remains for ink jet compositions and processes that enable rapid drying times while also providing good optical density characteristics. Additionally, a need remains for ink jet compositions and processes that enable rapid drying times while also providing good edge acuity characteristics. There is also a need for ink jet compositions and processes that enable rapid drying times while also providing good inter-color bleed characteristics.

SUMMARY OF THE INVENTION

The present invention is directed to an ink composition comprising a liquid ink vehicle, a colorant, and a cyclic siloxane monomer composition capable of undergoing a ring-opening polymerization process upon contact with an anionic base. Another embodiment of the present invention is directed to a process which comprises (a) providing (1) a first ink comprising water and at least one cyclic siloxane monomer composition; and (2) a second ink comprising a liquid ink vehicle and an anionic base capable of causing the cyclic siloxane monomer to polymerize upon contact therewith, wherein at least one of the first ink and the second ink further comprises a colorant (b) incorporating into an ink jet printing apparatus at least one of the first ink and the second ink; (c) applying the first ink onto a substrate; and (d) applying the second ink onto the substrate; wherein at least one of the first ink and the second ink is ejected from the ink jet printing apparatus in an imagewise pattern onto the substrate; and wherein the process results in at least some portions of the substrate bearing images formed from both the first ink and the second ink, said portions forming a printed image containing a polysiloxane and the colorant.

DETAILED DESCRIPTION OF THE INVENTION

The first and second ink compositions of the present invention contain a liquid vehicle. The liquid vehicle can consist solely of water, or it can be a nonaqueous vehicle comprising one or more organic liquids, or it can comprise a mixture of water and a water soluble or water miscible organic component, such as ethylene glycol, propylene glycol, diethylene glycols, glycerine, dipropylene glycols, polyethylene glycols, polypropylene glycols, amides, ethers, urea, substituted ureas, ethers, carboxylic acids and their salts, esters, alcohols, organosulfides, organosulfoxides, sulfones (such as sulfolane), alcohol derivatives, carbitol, butyl carbitol, cellusolve, tripropylene glycol monomethyl ether, ether derivatives, amino alcohols, ketones, N-methylpyrrolidinone, 2-pyrrolidinone, cyclohexylpyrrolidone, hydroxyethers, amides, sulfoxides, lactones, polyelectrolytes, methyl sulfonylethanol, imidazole, betaine, and other water soluble or water miscible materials, as well as mixtures thereof. When mixtures of water and water soluble or miscible organic liquids are selected as the liquid vehicle, the water to organic ratio typically ranges from about 100:0 to about 30:70, and preferably from about 97:3 to about 40:60, the non-water component of the liquid vehicle generally serves as a humectant or cosolvent which has a boiling point higher than that of water (100° C.). In the ink compositions of the present invention, the liquid vehicle is typically present in an amount of from about 80 to about 99.9 percent by weight of the ink, and preferably from about 90 to about 99 percent by weight of the ink, although the amount can be outside these ranges.

At least one of the first ink and the second ink of the present invention also contain a colorant. The colorant can be a dye, a pigment, or a mixture thereof. Examples of suitable dyes include anionic dyes, cationic dyes, nonionic dyes, zwitterionic dyes, and the like, Specific examples of suitable dyes include Food dyes such as Food Black No. 1, Food Black No. 2, Food Red No. 40, Food Blue No. 1, Food Yellow No. 7, and the like, FD & C dyes, Acid Black dyes (No. 1, 7, 9, 24, 26, 48, 52, 58, 60, 61, 63, 92, 107, 109, 118, 119, 131, 140, 155, 156, 172, 194, and the like), Acid Red dyes (No. 1, 8, 32, 35, 37, 52, 57, 92, 115, 119, 154, 249, 254, 256, and the like), Acid Blue dyes (No. 1, 7, 9, 25, 40, 45, 62, 78, 80, 92, 102, 104, 113, 117, 127, 158, 175, 183, 193, 209, and the like), Acid Yellow dyes (No. 3, 7, 17, 19, 23, 25, 29, 38, 42, 49, 59, 61, 72, 73, 114, 128, 151, and the like), Direct Black dyes (No. 4, 14, 17, 22, 27, 38, 51, 112, 117, 154, 168, and the like), Direct Blue dyes (No. 1, 6, 8, 14, 15, 25, 71, 76, 78, 80, 86, 90, 106, 108, 123, 163, 165, 199, 226, and the like), Direct Red dyes (No. 1, 2, 16, 23, 24, 28, 39, 62, 72, 236, and the like), Direct Yellow dyes (No. 4, 11, 12, 27, 28, 33, 34, 39, 50, 58, 86, 100, 106, 107, 118, 127, 132, 142, 157, and the like), anthraquinone dyes, monoazo dyes, disazo dyes, phthalocyanine derivatives, including various phthalocyanine sulfonate salts, aza(18) annulenes, formazan copper complexes, triphenodioxazines, Bernacid Red 2BMN; Pontamine Brilliant Bond Blue A; Pontamine; Caro direct Turquoise FBL Supra Conc. (Direct Blue 199), available from Carolina Color and Chemical; Special Fast Turquoise 8GL Liquid (Direct Blue 86), available from Mobay Chemical; Intrabond Liquid Turquoise GLL (Direct Blue 86), available from Crompton and Knowles; Cibracron Brilliant Red 38-A (Reactive Red 4), available from Aldrich Chemical; Drimarene Brilliant Red X-2B (Reactive Red 56), available from Pylam, Inc.; Levafix Brilliant Red E-4B, available from Mobay Chemical; Levafix Brilliant Red E-6BA, available from Mobay Chemical; Procion Red H8B (Reactive Red 31), available from ICI America; Pylam Certified D&C Red #28 (Acid Red 92), available from Pylam; Direct Brilliant Pink B Ground Crude, available from Crompton & Knowles; Cartasol Yellow GTF Presscake, available from Sandoz, Inc.; Tartrazine Extra Conc. (FD&C Yellow #5, Acid Yellow 23), available from Sandoz; Carodirect Yellow RL (Direct Yellow 86), available from Carolina Color and Chemical; Cartasol Yellow GTF Liquid Special 110, available from Sandoz, Inc.; D&C Yellow # 10 (Acid Yellow 3), available from Tricon; Yellow Shade 16948, available from Tricon, Basacid Black X34, available from BASF, Carta Black 2GT, available from Sandoz, Inc.; Neozapon Red 492 (BASF); Savinyl Blue GLS (Sandoz); Luxol Blue MBSN (Morton-Thiokol); Basacid Blue 750 (BASF); Bernacid Red, available from Berncolors, Poughkeepsie, N.Y.; Pontamine Brilliant Bond Blue; Berncolor A. Y. 34; Telon Fast Yellow 4GL-175, BASF Basacid Black SE 0228; the PRO-JET® series of dyes available from ICI, including PRO-JET® Yellow I (Direct Yellow 86), PRO-JET® Magenta I (Acid Red 249), PRO-JET® Cyan I (Direct Blue 199), PRO-JET® Black I (Direct Black 168), PRO-JET® Yellow 1-G (Direct Yellow 132), Aminyl Brilliant Red F-B, available from Sumitomo Chemical Company (Japan), the DUASYN® line of "salt-free" dyes available from Clariant Corp., Charlotte, N.C., such as DUASYN® Direct Black HEF-SF (Direct Black 168), DUASYN® Black RL-SF (Reactive Black 31), DUASYN® Direct Yellow 6G-SF VP216 (Direct Yellow 157), DUASYN® Brilliant Yellow GL-SF VP220 (Reactive Yellow 37), DUASYN® Acid Yellow XX-SF LP413 (Acid Yellow 23), DUASYN® Brilliant Red F3B-SF VP218 (Reactive Red 180), DUASYN® Rhodamine B-SF VP353 (Acid Red 52), DUASYN® Direct Turquoise Blue FRL-SF VP368 (Direct Blue 199), DUASYN® Acid Blue AE-SF VP344 (Acid Blue 9), Orasol Red G (Ciba-Geigy); Direct Brilliant Pink B (Crompton-Knolls); Aizen Spilon Red C-BH (Hodogaya Chemical Company); Kayanol Red 3BL (Nippon Kayaku Company); Levanol Brilliant Red 3BW (Mobay Chemical Company); Levaderm Lemon Yellow (Mobay Chemical Company); Spirit Fast Yellow 3G; Aizen Spilon Yellow C-GNH (Hodogaya Chemical Company); Sirius Supra Yellow GD 167; Cartasol Brilliant Yellow 4GF (Sandoz); Pergasol Yellow CGP (Ciba-Geigy); Orasol Black RL (Ciba-Geigy); Orasol Black RLP (Ciba-Geigy); Savinyl Black RLS (Sandoz); Dermacarbon 2GT (Sandoz); Pyrazol Black BG (ICI); Morfast Black Conc A (Morton-Thiokol), Diazol Black RN Quad (ICI); Orasol Blue GN (Ciba-Geigy); Sevron Blue 5GMF (ICI); various Reactive dyes, including Reactive Black dyes, Reactive Blue dyes, Reactive Red dyes, Reactive Yellow dyes, and the like, as well as mixtures thereof. The dye is present in the ink composition in any desired or effective amount, typically from about 0.05 to about 15 percent by weight of the ink, preferably from about 0.1 to about 10 percent by weight of the ink, and more preferably from about 1 to about 5 percent by weight of the ink, although the amount can be outside of these ranges.

Examples of suitable pigments include various carbon blacks such as channel black, furnace black, lamp black, and the like. Colored pigments include red, green, blue, brown, magenta, cyan, and yellow particles, as well as mixtures thereof. Illustrative examples of magenta pigments include 2,9-dimethyl-substituted quinacridone and anthraquinone dye, identified in the Color Index as CI 60710, CI Dispersed Red 15, a diazo dye identified in the Color Index as CI 26050, CI Solvent Red 19, and the like. Illustrative examples of suitable cyan pigments include copper tetra-4-(octadecyl sulfonamido) phthalocyanine, X-copper phthalocyanine pigment, listed in the Color Index as CI 74160, CI Pigment Blue, and Anthradanthrene Blue, identified in the Color Index as CI 69810, Special Blue X-2137, and the like. Illustrative examples of yellow pigments that can be selected include diarylide yellow 3,3-dichlorobenzidene acetoacetanilides, a monoazo pigment identified in the Color Index as CI 12700, CI Solvent Yellow 16, a nitrophenyl amine sulfonamide identified in the Color Index as Foron Yellow SE/GLN, CI Dispersed Yellow 33, 2,5-dimethoxy-4-sulfonanilide phenylazo-4'-chloro-2,5-dimethoxy acetoacetanilide, Permanent Yellow FGL, and the like. Additional examples of pigments include RAVEN® 5250, RAVEN® 5750, RAVEN® 3500 and other similar carbon black products available from Columbia Company, REGAL® 330, BLACK PEARL® L, BLACK PEARL® 1300, and other similar carbon black products available from Cabot Company, commercial carbon black dispersions such as CABOJET® 200, CABOJET® 300 (surface modified pigment), CABOJET® IJX 157, CABOJET® IJX 164, and the like, available from Cabot Chemical Co., the BON-JET® pigment dispersions from Orient Chemical Company of Japan, Degussa carbon blacks such as COLOR BLACK® series, SPECIAL BLACK® series, PRINTTEX® series and DERUSSOL® carbon black dispersions available from Degussa Company, HOSTAFINE® series such as HOSTAFINE® Yellow GR (Pigment 13), HOSTAFINE® Yellow (Pigment 83), HOSTAFINE® Red FRLL (Pigment Red 9), HOSTAFINE® Rubine F6B (Pigment 184), HOSTAFINE® Blue 2G (Pigment Blue 15:3), HOSTAFINE® Black T (Pigment Black 7), and HOSTAFINE® Black TS (Pigment Black 7), available from Clariant Corp., Charlotte, N.C., Normandy Magenta RD-2400 (Paul Uhlich), Paliogen Violet 5100 (BASF), Paliogen Violet 5890 (BASF), Permanent Violet VT2645 (Paul Uhlich), Heliogen Green L8730 (BASF), Argyle Green XP-111-S (Paul Uhlich), Brilliant Green Toner GR 0991 (Paul Uhlich), Heliogen Blue L6900, L7020 (BASF), Heliogen Blue D6840, D7080 (BASF), Sudan Blue OS (BASF), PV Fast Blue B2G01 (Clariant Corp., Charlotte, N.C.), Irgalite Blue BCA (Ciba-Geigy), Paliogen Blue 6470 (BASF), Sudan III (Matheson, Coleman, Bell), Sudan II (Matheson, Coleman, Bell), Sudan IV (Matheson, Coleman, Bell), Sudan Orange 6 (Aldrich), Sudan Orange G (Aldrich), Sudan Orange 220 (BASF), Paliogen Orange 3040 (BASF), Ortho Orange OR 2673 (Paul Uhlich), Paliogen Yellow 152, 1560 (BASF), Lithol Fast Yellow 0991K (BASF), Paliotol Yellow 1840 (BASF), Novoperm Yellow F6 1 (Clariant Corp., Charlotte, N.C.), Novoperm Yellow FG1 (Clariant Corp., Charlotte, N.C.), Permanent Yellow YE 0305 (Paul Uhlich), Lumogen Yellow D0790 (BASF), Suco-Gelb L1250 (BASF), Suco-Yellow D1355 (BASF), Hostaperm Pink E (Clariant Corp., Charlotte, N.C.), Fanal Pink D4830 (BASF), Cinquasia Magenta (DuPont), Lithol Scarlet D3700 (BASF), Tolidine Red (Aldrich), Scarlet for thermoplast NSD PS PA (Ugine Kuhlmann of Canada), E.D. Toluidine Red (Aldrich), Lithol Rubine Toner (Paul Uhlich), Lithol Scarlet 4440 (BASF), Bon Red C (Dominion Color Company), Royal Brilliant Red RD-8192 (Paul Uhlich), Oracet Pink RF (Ciba-Geigy), Paliogen Red 3871K (BASF), Paliogen Red 3340 (BASF), Lithol Fast Scarlet L4300 (BASF), CAB-O-JET® 200 hydrophilic carbon black (Cabot Corp.), CAB-O-JET® 300 hydrophilic carbon black (Cabot Corp.), and the like. Additional suitable commercially available pigment dispersions include the Hostafines available from Clariant Corp., Charlotte, N.C., including HOSTAFINE Yellow HR and HOSTAFINE Blue B2G, as well as dispersions available from BASF, including Disperse Black 00-6607, Luconyl Yellow 1250, Basoflex Pink 4810, Luconyl Blue 7050, and the like. Other pigments can also be selected. Preferably, the pigment particle size is as small as possible to enable a stable colloidal suspension of the particles in the liquid vehicle and to prevent clogging of the ink channels when the ink is used in a thermal ink jet printer. Preferred particle average diameters are generally from about 0.001 to about 5 microns, and more preferably from about 0.1 to about 1 micron, although the particle size can be outside these ranges. Within the ink compositions of the present invention, the pigment is present in any effective amount to achieve the desired degree of coloration. Typically, the pigment is present in an amount of from about 0.1 to about 8 percent by weight of the ink, and preferably from about 2 to about 7 percent by weight of the ink, although the amount can be outside these ranges.

At least one of the first and the second ink compositions contains at least one colorant. Typically, the colorant is in the first ink containing the cyclic siloxane monomer, thereby enabling the use of colorants that are not stable in a strongly alkaline solution. The colorant can, however, be present in the second ink containing the anionic base, provided that the colorant is stable and soluble or dispersible in an alkaline solution.

The first ink of the present invention contains a cyclic siloxane monomer composition. This cyclic siloxane monomer composition is one that is capable of undergoing a ring-opening polymerization upon contact with an anionic base. Suitable cyclic siloxane monomers include those of the formula

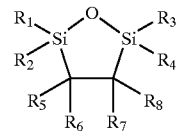

wherein $R_1$, $R_2$, $R_3$, and $R_4$ each, independently of the others, is an alkyl group (including linear, branched, saturated, unsaturated, cyclic, and substituted alkyl groups, and wherein hetero atoms, such as oxygen, silicon, and the like can be present in the alkyl group), typically with from 1 to about 30 carbon atoms, preferably with from 1 to about 20 carbon atoms, and more preferably with from 1 to about 12 carbon atoms, although the number of carbon atoms can be outside of these ranges, an aryl group (including substituted aryl groups), typically with from about 6 to about 30 carbon atoms, preferably with from about 6 to about 20 carbon atoms, and more preferably with from about 6 to about 10 carbon atoms, although the number of carbon atoms can be outside of these ranges, an arylalkyl group (including substituted arylalkyl groups), typically with from about 7 to about 30 carbon atoms, preferably with from about 7 to about 20 carbon atoms, and more preferably with from about 7 to about 14 carbon atoms, although the number of carbon atoms can be outside of these ranges, such as benzyl or the like, an alkylaryl group (including substituted alkylaryl groups), typically with from about 7 to about 30 carbon atoms, preferably with from about 7 to about 20 carbon atoms, and more preferably with from about 7 to about 14 carbon atoms, although the number of carbon atoms can be outside of these ranges, an alkoxy group (including substituted alkoxy groups, and wherein hetero atoms, such as oxygen, silicon, and the like can be present in the alkoxy group), typically with from 1 to about 30 carbon atoms, preferably with from 1 to about 20 carbon atoms, and more preferably with from 1 to about 12 carbon atoms, although the number of carbon atoms can be outside of these ranges, a polyalkyleneoxy group, such as polyethyleneoxy groups, polypropyleneoxy groups, polybutyleneoxy groups, and the like, typically with from about 2 to about 60 repeat alkyleneoxy units, preferably with from about 2 to about 30 repeat alkyleneoxy units, and more preferably with from about 2 to about 20 repeat alkyleneoxy units, although the number of repeat alkyleneoxy units can be outside of these ranges, and $R_5$, $R_6$, $R_7$, and $R_8$ each, independently of the others, is a hydrogen atom, an alkyl group (including linear, branched, saturated, unsaturated, cyclic, and substituted alkyl groups, and wherein hetero atoms, such as oxygen, silicon, and the like can be present in the alkyl group), typically with from 1 to about 30 carbon atoms, preferably with from 1 to about 20 carbon atoms, and more preferably with from 1 to about 12 carbon atoms, although the number of carbon atoms can be outside of these ranges, an aryl group (including substituted aryl groups), typically with from about 6 to about 30 carbon atoms, preferably with from about 6 to about 20 carbon atoms, and more preferably with from about 6 to about 12 carbon atoms, although the number of carbon atoms can be outside of these ranges, an arylalkyl group (including substituted arylalkyl groups), typically with from about 7 to about 30 carbon atoms, preferably with from about 7 to about 20 carbon atoms, and more preferably with from about 7 to about 14 carbon atoms, although the number of carbon atoms can be outside of these ranges, such as benzyl or the like, an alkylaryl group (including substituted alkylaryl groups), typically with from about 7 to about 30 carbon atoms, preferably with from about 7 to about 20 carbon atoms, and more preferably with from about 7 to about 14 carbon atoms, although the number of carbon atoms can be outside of these ranges, an alkoxy group (including substituted alkoxy groups, and wherein hetero atoms, such as oxygen, silicon, and the like can be present in the alkoxy group), typically with from 1 to about 30 carbon atoms, preferably with from 1 to about 20 carbon atoms, and more preferably with from 1 to about 12 carbon atoms, although the number of carbon atoms can be outside of these ranges, a polyalkyleneoxy group, such as polyethyleneoxy groups, polypropyleneoxy groups, polybutyleneoxy groups, and the like, typically with from about 2 to about 60 repeat alkyleneoxy units, preferably with from about 2 to about 30 repeat alkyleneoxy units, and more preferably with from about 2 to about 20 repeat alkyleneoxy units, although the number of repeat alkyleneoxy units can be outside of these ranges, wherein two or more of $R_1$, $R_2$, $R_3$, $R_4$, $R_5$, $R_6$, $R_7$, and/or $R_8$ can be joined together to form a ring, and wherein the substituents on the substituted alkyl, aryl, arylalkyl, alkylaryl, alkoxy, and polyalkyleneoxy groups can be (but are not limited to) hydroxy groups, amine groups, ammonium groups, cyano groups, pyridine groups, pyridinium groups, ether groups, aldehyde groups, ketone groups, ester groups, amide groups, carbonyl groups, sulfide groups, sulfoxide groups, phosphine groups, phosphonium groups, nitrile groups, mercapto groups, nitroso groups, halogen atoms, nitro groups, sulfone groups, acyl groups, mixtures thereof, and the like, wherein two or more substituents can be joined together to form a ring.

Specific examples of suitable cyclic siloxane monomers include those of the formulae

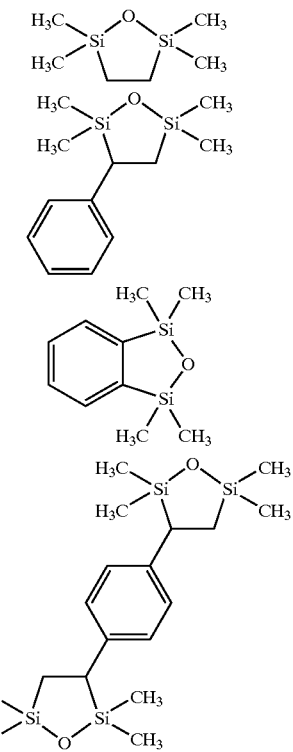

and the like, as well as mixtures thereof, 2,2,5,5-Tetramethyl-2,5-dislaoxacyclopentane is commercially available from Gelest, Inc. of Tullytown, Pa. The phenylene bridged bis-cyclic siloxane can be synthesized as described by Loy, et al. and shown in the scheme below by the reaction of 1,4-diethynylbenzene with tetramethyldimethoxydisilane $(CH_3)_4Si_2(OCH_3)_2$, catalyzed by palladium-triphenylphosphine, $(Pd(PPh_3)_4)$ (Strem Chemical), followed by acid catalyzed ring closure and hydrogenation of the intermediate disilaoxacyclopentane:

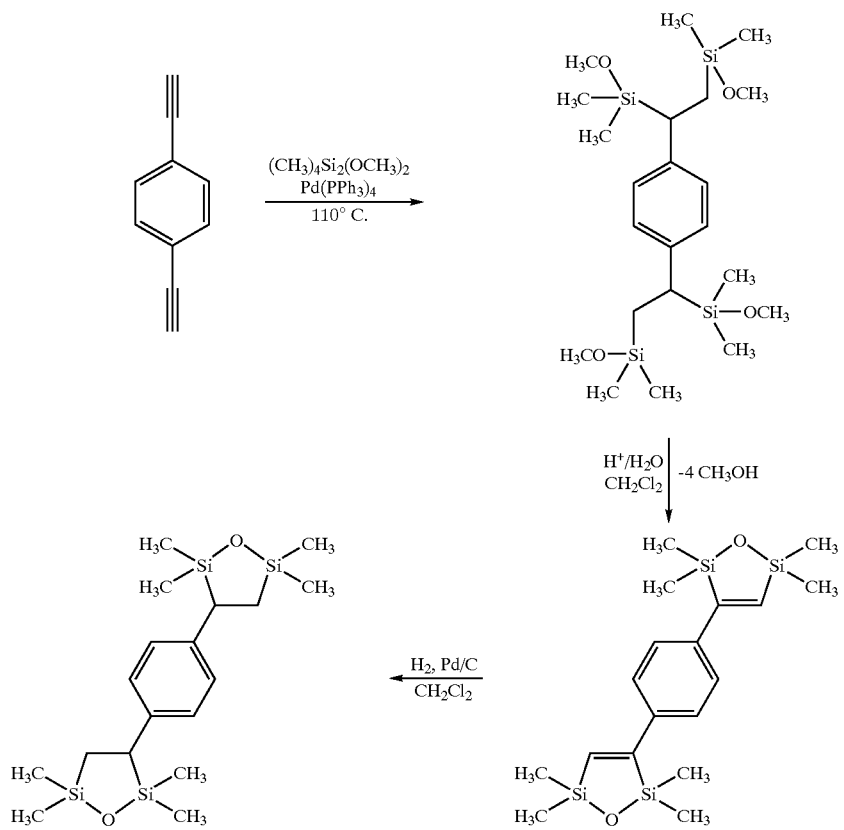

3-Phenyl-2,2,5,5-tetramethyl-2,5-dislaoxacyclopentane can be synthesized in an analogous manner, starting from phenylacetylene.

The cyclic siloxane monomer composition is present in the first ink in any desired or effective amount, typically at least about 5 percent by weight of the ink, preferably at least about 20 percent by weight of the ink, and more preferably at least about 40 percent by weight of the ink, and typically no more than about 99 percent by weight of the ink, preferably no more than about 95 percent by weight of the ink, and more preferably no more than about 90 percent by weight of the ink, although the amount can be outside of these ranges.

The second ink of the present invention contains an anionic base capable of causing the cyclic siloxane monomer composition to undergo a ring-opening polymerization upon contact of the anionic base with the cyclic siloxane monomer. Examples of suitable anionic bases include tetraalkylammonium hydroxides, such as tetrabutylammonium hydroxide and the like.

The anionic base is present in the second ink in any desired or effective amount, typically at least about 1 percent by weight of the ink, preferably at least about 2 percent by weight of the ink, and more preferably at least about 5 percent by weight of the ink, and typically no more than about 20 percent by weight of the ink, preferably no more than about 15 percent by weight of the ink, and more preferably no more than about 10 percent by weight of the ink, although the amount can be outside of these ranges.

When the first ink and the second ink are jetted onto a substrate, the anionic base contacts the cyclic siloxane monomer, causing a rapid ring-opening polymerization of the cyclic siloxane monomer. For example, when the monomer is of the formula

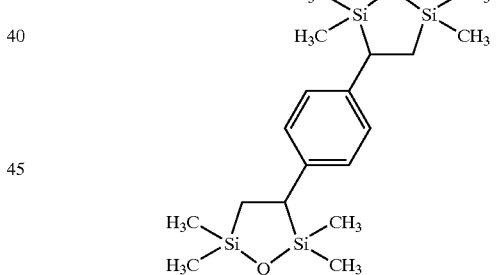

upon contact with the anionic base, the monomer polymerizes as follows:

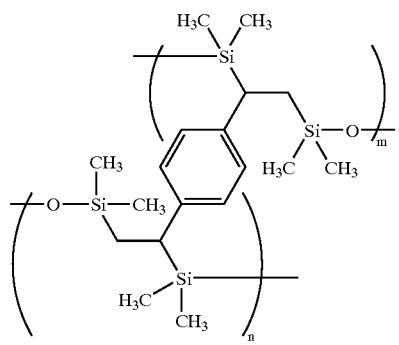

The order of deposition of the first ink and the second ink is unimportant. Either the first ink or the second ink can be applied to the substrate first, followed by application of the other ink; the first ink and the second ink can also be applied simultaneously to the substrate.

At least one of the first ink and the second ink is applied to the substrate in an imagewise pattern. In one specific embodiment, both the first ink and the second ink are applied to the substrate in an imagewise pattern. In another specific embodiment, one of the first ink and the second ink is applied to the substrate in an imagewise pattern and the other of the first ink and the second ink is applied uniformly to the substrate. In some instances, it can be preferred to apply the first ink to the substrate in an imagewise pattern and to apply the second ink uniformly to the substrate, although it is also contemplated that one can apply the second ink to the substrate in an imagewise pattern and apply the first ink uniformly to the substrate.

Uniform deposition of an ink to the substrate can be performed in any desired or effective method, such as by jetting it from an ink jet printing apparatus, applying it from a donor roll or other applicator, or the like. One example of a suitable apparatus for applying an ink uniformly to a substrate is disclosed in U.S. Pat. No. 6,142,618, the disclosure of which is totally incorporated herein by reference.

By "substrate" is meant either a final recording sheet, such as paper, transparency material, and the like, or one or more intermediate transfer members onto which the inks are first applied, followed by transferring the inks to a final recording sheet.

When used in ink jet printing applications, the first and second ink compositions according to the present invention are generally of a viscosity suitable for use in said ink jet printing processes. For example, for thermal ink jet printing applications, at room temperature (i.e., about 25° C.), typically, the ink viscosity is typically at least about 1 centipoise and typically is no more than about 10 centipoise, preferably no more than about 7 centipoise, and more preferably no more than about 5 centipoise, although the viscosity can be outside of these ranges, particularly when the ink is used for applications such as acoustic ink jet printing.

The first and second ink compositions can be prepared by any suitable process. Typically, the inks are prepared by simple mixing of the ingredients. One process entails mixing all of the ink ingredients together and filtering the mixture to obtain an ink. Inks can be prepared by mixing the ingredients, heating if desired, and filtering, followed by adding any desired additional additives to the mixture and mixing at room temperature with moderate shaking until a homogeneous mixture is obtained, typically from about 5 to about 10 minutes. Alternatively, the optional ink additives can be mixed with the other ink ingredients during the ink preparation process, which takes place according to any desired procedure, such as by mixing all the ingredients, heating if desired, and filtering.

The ink compositions of the present invention can be used in a process which entails incorporating the ink composition into an ink jet printing apparatus and causing droplets of the ink composition to be ejected in an imagewise pattern onto a substrate. In a particularly preferred embodiment, the printing apparatus employs a thermal ink jet process wherein the ink in the nozzles is selectively heated in an imagewise pattern, thereby causing droplets of the ink to be ejected in imagewise pattern. In another embodiment, the printing apparatus employs an acoustic ink jet process wherein droplets of the ink are caused to be ejected in imagewise pattern by acoustic beams. In yet another embodiment, the printing apparatus employs a piezoelectric ink jet process, wherein droplets of the ink are caused to be ejected in imagewise pattern by oscillations of piezoelectric vibrating elements. Any suitable substrate can be employed, including plain papers such as Xerox® 4024 papers, Xerox® Image Series papers, Courtland 4024 DP paper, ruled notebook paper, bond paper, silica coated papers such as Sharp Company silica coated paper, JuJo paper, and the like, transparency materials, fabrics, textile products, plastics, polymeric films, inorganic substrates such as metals and wood, and the like. In a preferred embodiment, the process entails printing onto a porous or ink absorbent substrate, such as plain paper.

The present invention can employ any suitable or desired ink jet printing apparatus, including continuous stream ink jet printers, piezoelectric ink jet printers, thermal ink jet printers, acoustic ink jet printers, hot melt ink jet printers of any of the above types, or the like. Examples of suitable ink jet printers and printheads are disclosed in, for example, Copending application U.S. Ser. No. 09/152,100, U.S. Pat. Nos. 4,638,337, 4,601,777, 5,739,254, 5,753,783, 4,678,529, 4,567,493, 4,568,953, 4,789,425, 4,985,710, 5,160,945, 4,935,750, Re. 32,572, 5,185,614, 4,771,295, 4,697,195, 5,568,169, 5,565,113, 5,596,355, 5,371,531, 4,797,693, 5,198,054, 5,971,531, 6,079,814, and 5,486,855, the disclosures of each of which are totally incorporated herein by reference.

Specific embodiments of the invention will now be described in detail. These examples are intended to be illustrative, and the invention is not limited to the materials, conditions, or process parameters set forth in these embodiments. All parts and percentages are by weight unless otherwise indicated.

EXAMPLE I

An ink composition according to the present invention is prepared by simple mixing of 30 parts by weight of 3-phenyl-2,2,5,5-tetramethyl-2,5-disilaoxacyclopentane, 20 parts by weight of tetramethyldisilafuran, and 10 parts by weight of 1,4-bis-(3-phenyl)-2,2,5,5-tetramethyl-2,5-disilaoxacyclopentane with 15 parts by weight of propylene glycol, 10 parts by weight of 2-pyrrolidone, 10 parts by weight of ACRYLJET® Black-357 aqueous carbon black dispersion (Rohm & Haas, Philadelphia, Pa.) and 5 parts by weight of water.

EXAMPLE II

An ink composition for the present invention is prepared by simple mixing of 20 parts by weight of tetrabutylammonium hydroxide (40 percent by weight aqueous solution, Aldrich 42,632-6), with 30 parts by weight of propylene glycol, 30 parts by weight of 2-pyrrolidone, and 20 parts by weight of water.

EXAMPLE III

The ink compositions of Example I and Example II are incorporated into separate cartridges of a XEROX® M-750 ink jet printer and applied in an imagewise pattern to a paper substrate so that the resulting images contain the colorant of the ink of Example I and a polysiloxane formed from the cyclic siloxane monomers in the ink of Example I.

EXAMPLE IV

The ink composition of Example II is applied uniformly to a paper substrate with a donor apparatus as described in U.S. Pat. No. 6,142,618, the disclosure of which is totally incorporated herein by reference. Thereafter, the ink composition of Example I is printed from a XEROX® M-750 ink jet printer onto the substrate so that the resulting images contain the colorant of the ink of Example I and a polysiloxane formed from the cyclic siloxane monomers in the ink of Example I.

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. An ink composition comprising a liquid ink vehicle, a colorant, and a cyclic siloxane monomer composition capable of undergoing a ring-opening polymerization process upon contact with an anionic base.

2. An ink composition according to claim 1 wherein the cyclic siloxane monomer is of the formula

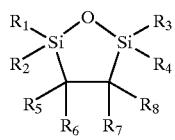

wherein $R_1$, $R_2$, $R_3$, and $R_4$ each, independently of the others, is an alkyl group, an aryl group, an arylalkyl group, an alkylaryl group, an alkoxy group, or a polyalkyleneoxy group, wherein $R_5$, $R_6$, $R_7$, and $R_8$ each, independently of the others, is a hydrogen atom, an alkyl group, an aryl group, an arylalkyl group, an alkylaryl group, an alkoxy group, or a polyalkyleneoxy group, and wherein two or more of $R_1$, $R_2$, $R_3$, $R_4$, $R_5$, $R_6$, $R_7$, and/or $R_8$ can be joined together to form a ring.

3. An ink composition according to claim 1 wherein the cyclic siloxane monomer is selected from

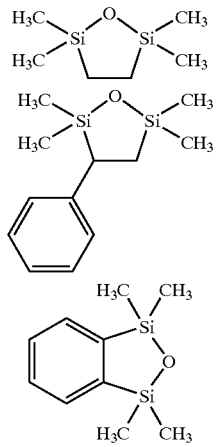

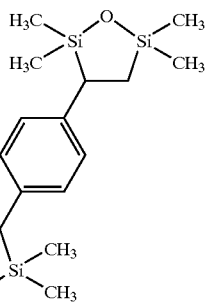

or mixtures thereof.

4. An ink composition according to claim 1 wherein the cyclic siloxane monomer is present in the ink in an amount of at least about 5 percent by weight of the ink, and wherein the cyclic siloxane monomer is present in the ink in an amount of no more than about 99 percent by weight of the ink.

5. An ink composition comprising a liquid ink vehicle, a colorant and a cyclic siloxane monomer composition capable of undergoing a ring-opening polymerization process upon contact with an anionic base wherein the anionic base is a tetraalkylammonium hydroxide.

6. An ink composition according to claim 5 wherein the anionic base is tetrabutylammonium hydroxide.

7. An ink set which comprises (a) a first ink composition comprising a liquid ink vehicle and a cyclic siloxane monomer composition capable of undergoing a ring-opening polymerization process upon contact with an anionic base, and (b) a second ink composition comprising a liquid ink vehicle and an anionic base capable of causing the cyclic siloxane monomer to polymerize upon contact therewith, wherein at least one of the first ink and the second ink further comprises a colorant.

8. A process which comprises (a) providing (1) a first ink comprising water and at least one cyclic siloxane monomer composition; and (2) a second ink comprising a liquid ink vehicle and an anionic base capable of causing the cyclic siloxane monomer to polymerize upon contact therewith, wherein at east one of the first ink and the second ink further comprises a colorant; (b) incorporating into an ink jet printing apparatus at least one of the first ink and the second ink; (c) applying the first ink onto a substrate; and (d) applying the second ink onto the substrate; wherein at least one of the first ink and the second ink is ejected from the ink jet printing apparatus in an imagewise pattern onto the substrate; and wherein the process results in at least some portions of the substrate bearing images formed from both the first ink and the second ink, said portions forming a printed image containing a polysiloxane and the colorant.

9. A process according to claim 8 wherein the cyclic siloxane monomer is of the formula

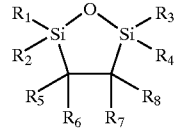

wherein $R_1$, $R_2$, $R_3$, and $R_4$ each, independently of the others, is an alkyl group, an aryl group, an arylalkyl group, an alkylaryl group, an alkoxy group, or a polyalkyleneoxy group, wherein $R_5$, $R_6$, $R_7$, and $R_8$ each, independently of the others, is a hydrogen atom, an alkyl group, on aryl group, an arylalkyl group, an alkylaryl group an alkoxy group, or a polyalkyleneoxy group, and wherein two or more of $R_1$, $R_2$, $R_3$, $R_4$, $R_5$, $R_6$, $R_7$, and/or $R_8$ can be Joined together to form a ring.

10. A process according to claim 8 wherein the cyclic siloxane monomer is selected from

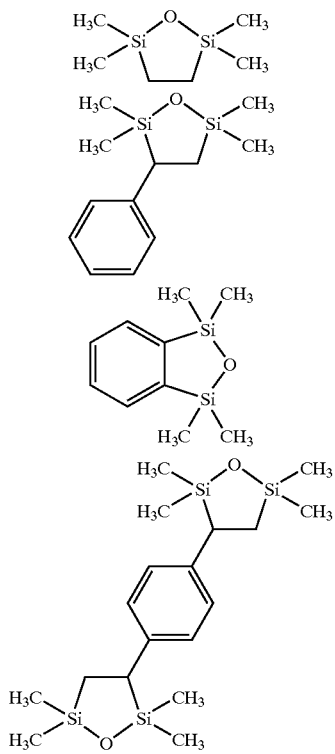

or mixtures thereof.

11. A process according to claim 8 wherein the cyclic siloxane monomer is present in the first ink in an amount of at least about 5 percent by weight of the first ink, and wherein the cyclic siloxane monomer is present in the first ink in an amount of no more than about 99 percent by weight of the first ink.

12. A process according to claim 8 wherein the anionic base is a tetraalkylammonium hydroxide.

13. A process according to claim 8 wherein the anionic base is present in the second ink in an amount of at least about 1 percent by weight of the second ink, and wherein the anionic base is present in the second ink in an amount of no mare than about 20 percent by weight of the second ink.

14. A process according to claim 8 wherein the colorant is present in the first ink.

15. A process according to claim 8 wherein the colorant is present in the second ink.

16. A process according to claim 8 wherein the first ink is applied to the substrate in an imagewise pattern.

17. A process according to claim 8 wherein the second ink is applied to the substrate in an imagewise pattern.

18. A process according to claim 8 wherein both the first ink and the second ink are applied to the substrate in an imagewise pattern.

19. A process according to claim 8 wherein the substrate is a final recording sheet.

20. A process according to claim 8 wherein the substrate is an intermediate transfer member and the image is transferred from the intermediate transfer member to a final recording sheet.

* * * * *